(12) United States Patent
Achen et al.

(10) Patent No.: US 6,689,352 B2
(45) Date of Patent: Feb. 10, 2004

(54) METHOD FOR ACTIVATING ONLY THE VASCULAR ENDOTHELIAL GROWTH FACTOR RECEPTOR-3 AND USES THEREOF

(75) Inventors: Marc Achen, Parkville (AU); Steven Stacker, Parkville (AU)

(73) Assignee: Ludwig Institute for Cancer Research, New York, NY (US)

( * ) Notice: Subject to any disclaimer, the term of this patent is extended or adjusted under 35 U.S.C. 154(b) by 0 days.

(21) Appl. No.: 09/847,524

(22) Filed: May 3, 2001

(65) Prior Publication Data

US 2003/0166523 A1 Sep. 4, 2003

Related U.S. Application Data

(60) Provisional application No. 60/201,421, filed on May 3, 2000.

(51) Int. Cl.⁷ ................................................ A61K 38/19
(52) U.S. Cl. ...................................... 424/85.1; 530/351
(58) Field of Search ....................... 424/85.1; 530/351; 435/7.1, 325

(56) References Cited

PUBLICATIONS

Achen et al. VEGF–D is a ligand for the VEGF receptor 2 (Flk1) and VEGF receptor 3 (Flt4). 1998. Proc. Natl. Acad. Sci. USA, 95:548–553.*

* cited by examiner

*Primary Examiner*—Lorraine Spector
*Assistant Examiner*—Dong Jiang
(74) *Attorney, Agent, or Firm*—Crowell & Moring LLP

(57) ABSTRACT

A method for activating only the vascular endothelial growth factor receptor-3 has been created. The method comprises administration of a composition comprising a polypeptide to an animal wherein the composition has the ability to stimulate one or more lymphatic vessel endothelial cells to proliferate, differentiate, migrate, or survive. Methods are also provided to selectively activate a VEGF receptor-3, to screen for neoplastic disease characterized by an increase in lymph vessel endothelial cells, and to identify lymph vessel endothelial cells.

10 Claims, 4 Drawing Sheets

SEQUENCE LISTING

<160> NUMBER OF SEQ ID NOS: 6

<210> SEQ ID NO 1
<211> LENGTH: 1325
<212> TYPE: DNA
<213> ORGANISM: Murinae gen. sp.
<220> FEATURE:
<221> NAME/KEY: CDS
<222> LOCATION: (82)..(1155)

<400> SEQUENCE: 1

```
ggagaatgcc ttttgcaaca cttttcagta gctgcctgga aacaactgct tagtcatcgg      60
tagacattta aaatattcaa a atg tat gga gaa tgg gga atg ggg aat atc       111
                       Met Tyr Gly Glu Trp Gly Met Gly Asn Ile
                        1               5                   10 ctc atg atg ttc cat gtg tac ttg gtg cag ggc ttc agg agc gaa cat       159
Leu Met Met Phe His Val Tyr Leu Val Gln Gly Phe Arg Ser Glu His
             15                  20                  25 gga cca gtg aag gat ttt tct ttt gag cga tca tcc cgg tcc atg ttg       207
Gly Pro Val Lys Asp Phe Ser Phe Glu Arg Ser Ser Arg Ser Met Leu
         30                  35                  40 gaa cga tct gaa caa cag atc cga gca gct tct agt ttg gag gag ttg       255
Glu Arg Ser Glu Gln Gln Ile Arg Ala Ala Ser Ser Leu Glu Glu Leu
     45                  50                  55 ctg caa atc gcg cac tct gag gac tgg aag ctg tgg cga tgc cgg ttg       303
Leu Gln Ile Ala His Ser Glu Asp Trp Lys Leu Trp Arg Cys Arg Leu
 60                  65                  70 aag ctc aaa agt ctt gcc agt atg gac tca cgc tca gca tcc cat cgc       351
Lys Leu Lys Ser Leu Ala Ser Met Asp Ser Arg Ser Ala Ser His Arg
 75                  80                  85                  90 tcc acc aga ttt gcg gca act ttc tat gac act gaa aca cta aaa gtt       399
Ser Thr Arg Phe Ala Ala Thr Phe Tyr Asp Thr Glu Thr Leu Lys Val
                 95                 100                 105 ata gat gaa gaa tgg cag agg acc caa tgc agc cct aga gag aca tgc       447
Ile Asp Glu Glu Trp Gln Arg Thr Gln Cys Ser Pro Arg Glu Thr Cys
            110                 115                 120 gta gaa gtc gcc agt gag ctg ggg aag aca acc aac aca ttc ttc aag       495
Val Glu Val Ala Ser Glu Leu Gly Lys Thr Thr Asn Thr Phe Phe Lys
        125                 130                 135 ccc ccc tgt gta aat gtc ttc cgg tgt gga ggc tgc tgc aac gaa gag       543
Pro Pro Cys Val Asn Val Phe Arg Cys Gly Gly Cys Cys Asn Glu Glu
    140                 145                 150 ggt gtg atg tgt atg aac aca agc acc tcc tac atc tcc aaa cag ctc       591
Gly Val Met Cys Met Asn Thr Ser Thr Ser Tyr Ile Ser Lys Gln Leu
155                 160                 165                 170 ttt gag ata tca gtg cct ctg aca tca gtg ccc gag tta gtg cct gtt       639
Phe Glu Ile Ser Val Pro Leu Thr Ser Val Pro Glu Leu Val Pro Val
                175                 180                 185 aaa att gcc aac cat acg ggt tgt aag tgc ttg ccc acg ggc ccc cgc       687
Lys Ile Ala Asn His Thr Gly Cys Lys Cys Leu Pro Thr Gly Pro Arg
            190                 195                 200
```

-continued

```
cat cct tac tca att atc aga aga tcc att cag acc cca gaa gaa gat      735
His Pro Tyr Ser Ile Ile Arg Arg Ser Ile Gln Thr Pro Glu Glu Asp
        205                 210                 215 gaa tgt cct cat tcc aag aaa ctc tgt cct att gac atg ctg tgg gat      783
Glu Cys Pro His Ser Lys Lys Leu Cys Pro Ile Asp Met Leu Trp Asp
220                 225                 230 aac acc aaa tgt aaa tgt gtt ttg caa gac gag act cca ctg cct ggg      831
Asn Thr Lys Cys Lys Cys Val Leu Gln Asp Glu Thr Pro Leu Pro Gly
235                 240                 245                 250 aca gaa gac cac tct tac ctc cag gaa ccc act ctc tgt gga ccg cac      879
Thr Glu Asp His Ser Tyr Leu Gln Glu Pro Thr Leu Cys Gly Pro His
            255                 260                 265 atg acg ttt gat gaa gat cgc tgt gag tgc gtc tgt aaa gca cca tgt      927
Met Thr Phe Asp Glu Asp Arg Cys Glu Cys Val Cys Lys Ala Pro Cys
        270                 275                 280 ccg gga gat ctc att cag cac ccg gaa aac tgc agt tgc ttt gag tgc      975
Pro Gly Asp Leu Ile Gln His Pro Glu Asn Cys Ser Cys Phe Glu Cys
        285                 290                 295 aaa gaa agt ctg gag agc tgc tgc caa aag cac aag att ttt cac cca     1023
Lys Glu Ser Leu Glu Ser Cys Cys Gln Lys His Lys Ile Phe His Pro
300                 305                 310 gac acc tgc agc tgt gag gac aga tgt cct ttt cac acc aga aca tgt     1071
Asp Thr Cys Ser Cys Glu Asp Arg Cys Pro Phe His Thr Arg Thr Cys
315                 320                 325                 330 gca agt aga aag cca gcc tgt gga aag cac tgg cgc ttt cca aag gag     1119
Ala Ser Arg Lys Pro Ala Cys Gly Lys His Trp Arg Phe Pro Lys Glu
            335                 340                 345 aca agg gcc cag gga ctc tac agc cag gag aac cct tgattcaact          1165
Thr Arg Ala Gln Gly Leu Tyr Ser Gln Glu Asn Pro
        350                 355 tcctttcaag tcccccatc tctgtcattt taaacagctc actgctttgt caagttgctg    1225
tcactgttgc ccactacccc ttgaacatgt gcaaacacag acacacacac acacacacac    1285
acagagcaac tagaattatg ttttctaggt gctgcctaag                         1325

<210> SEQ ID NO 2
<211> LENGTH: 358
<212> TYPE: PRT
<213> ORGANISM: Murinae gen. sp.

<400> SEQUENCE: 2

Met Tyr Gly Glu Trp Gly Met Gly Asn Ile Leu Met Met Phe His Val
1               5                   10                  15

Tyr Leu Val Gln Gly Phe Arg Ser Glu His Gly Pro Val Lys Asp Phe
            20                  25                  30

Ser Phe Glu Arg Ser Ser Arg Ser Met Leu Glu Arg Ser Glu Gln Gln
        35                  40                  45

Ile Arg Ala Ala Ser Ser Leu Glu Glu Leu Leu Gln Ile Ala His Ser
    50                  55                  60

Glu Asp Trp Lys Leu Trp Arg Cys Arg Leu Lys Leu Lys Ser Leu Ala
65                  70                  75                  80

Ser Met Asp Ser Arg Ser Ala Ser His Arg Ser Thr Arg Phe Ala Ala
                85                  90                  95

Thr Phe Tyr Asp Thr Glu Thr Leu Lys Val Ile Asp Glu Glu Trp Gln
            100                 105                 110

Arg Thr Gln Cys Ser Pro Arg Glu Thr Cys Val Glu Val Ala Ser Glu
        115                 120                 125

Leu Gly Lys Thr Thr Asn Thr Phe Phe Lys Pro Pro Cys Val Asn Val
```

-continued

```
            130                 135                 140
Phe Arg Cys Gly Gly Cys Cys Asn Glu Glu Gly Val Met Cys Met Asn
145                 150                 155                 160

Thr Ser Thr Ser Tyr Ile Ser Lys Gln Leu Phe Glu Ile Ser Val Pro
                165                 170                 175

Leu Thr Ser Val Pro Glu Leu Val Pro Val Lys Ile Ala Asn His Thr
            180                 185                 190

Gly Cys Lys Cys Leu Pro Thr Gly Pro Arg His Pro Tyr Ser Ile Ile
        195                 200                 205

Arg Arg Ser Ile Gln Thr Pro Glu Glu Asp Glu Cys Pro His Ser Lys
    210                 215                 220

Lys Leu Cys Pro Ile Asp Met Leu Trp Asp Asn Thr Lys Cys Lys Cys
225                 230                 235                 240

Val Leu Gln Asp Glu Thr Pro Leu Pro Gly Thr Glu Asp His Ser Tyr
                245                 250                 255

Leu Gln Glu Pro Thr Leu Cys Gly Pro His Met Thr Phe Asp Glu Asp
            260                 265                 270

Arg Cys Glu Cys Val Cys Lys Ala Pro Cys Pro Gly Asp Leu Ile Gln
        275                 280                 285

His Pro Glu Asn Cys Ser Cys Phe Glu Cys Lys Glu Ser Leu Glu Ser
    290                 295                 300

Cys Cys Gln Lys His Lys Ile Phe His Pro Asp Thr Cys Ser Cys Glu
305                 310                 315                 320

Asp Arg Cys Pro Phe His Thr Arg Thr Cys Ala Ser Arg Lys Pro Ala
                325                 330                 335

Cys Gly Lys His Trp Arg Phe Pro Lys Glu Thr Arg Ala Gln Gly Leu
            340                 345                 350

Tyr Ser Gln Glu Asn Pro
        355

<210> SEQ ID NO 3
<211> LENGTH: 1135
<212> TYPE: DNA
<213> ORGANISM: Murinae gen. sp.
<220> FEATURE:
<221> NAME/KEY: CDS
<222> LOCATION: (95)..(1057)

<400> SEQUENCE: 3
aaactttgct tctggagaat gccttttgca acacttttca gtagctgcct ggaaacaact      60
gcttagtcat cggtagacat ttaaaatatt caaa atg tat gga gaa tgg gga atg     115
                                    Met Tyr Gly Glu Trp Gly Met
                                      1               5 ggg aat atc ctc atg atg ttc cat gtg tac ttg gtg cag ggc ttc agg       163
Gly Asn Ile Leu Met Met Phe His Val Tyr Leu Val Gln Gly Phe Arg
         10                  15                  20 agc gaa cat gga cca gtg aag cga tca tcc cgg tcc atg ttg gaa cga       211
Ser Glu His Gly Pro Val Lys Arg Ser Ser Arg Ser Met Leu Glu Arg
     25                  30                  35 tct gaa caa cag atc cga gca gct tct agt ttg gag gag ttg ctg caa       259
Ser Glu Gln Gln Ile Arg Ala Ala Ser Ser Leu Glu Glu Leu Leu Gln
 40                  45                  50                  55 atc gcg cac tct gag gac tgg aag ctg tgg cga tgc cgg ttg aag ctc       307
Ile Ala His Ser Glu Asp Trp Lys Leu Trp Arg Cys Arg Leu Lys Leu
                 60                  65                  70 aaa agt ctt gcc agt atg gac tca cgc tca gca tcc cat cgc tcc acc       355
Lys Ser Leu Ala Ser Met Asp Ser Arg Ser Ala Ser His Arg Ser Thr
```

| | | | | | | | | | | | | | | | |
|---|---|---|---|---|---|---|---|---|---|---|---|---|---|---|---|
| | | 75 | | | | 80 | | | | | 85 | | | | |
| aga | ttt | gcg | gca | act | ttc | tat | gac | act | gaa | aca | cta | aaa | gtt | ata | gat | 403
| Arg | Phe | Ala | Ala | Thr | Phe | Tyr | Asp | Thr | Glu | Thr | Leu | Lys | Val | Ile | Asp |
| | | 90 | | | | | 95 | | | | 100 | | | | |

```
aga ttt gcg gca act ttc tat gac act gaa aca cta aaa gtt ata gat      403
Arg Phe Ala Ala Thr Phe Tyr Asp Thr Glu Thr Leu Lys Val Ile Asp
         90                  95                 100 gaa gaa tgg cag agg acc caa tgc agc cct aga gag aca tgc gta gaa      451
Glu Glu Trp Gln Arg Thr Gln Cys Ser Pro Arg Glu Thr Cys Val Glu
105                 110                 115 gtc gcc agt gag ctg ggg aag aca acc aac aca ttc ttc aag ccc ccc      499
Val Ala Ser Glu Leu Gly Lys Thr Thr Asn Thr Phe Phe Lys Pro Pro
120             125                 130                 135 tgt gta aat gtc ttc cgg tgt gga ggc tgc tgc aac gaa gag ggt gtg      547
Cys Val Asn Val Phe Arg Cys Gly Gly Cys Cys Asn Glu Glu Gly Val
            140                 145                 150 atg tgt atg aac aca agc acc tcc tac atc tcc aaa cag ctc ttt gag      595
Met Cys Met Asn Thr Ser Thr Ser Tyr Ile Ser Lys Gln Leu Phe Glu
                155                 160                 165 ata tca gtg cct ctg aca tca gtg ccc gag tta gtg cct gtt aaa att      643
Ile Ser Val Pro Leu Thr Ser Val Pro Glu Leu Val Pro Val Lys Ile
            170                 175                 180 gcc aac cat acg ggt tgt aag tgc ttg ccc acg ggc ccc cgc cat cct      691
Ala Asn His Thr Gly Cys Lys Cys Leu Pro Thr Gly Pro Arg His Pro
185                 190                 195 tac tca att atc aga aga tcc att cag acc cca gaa gaa gat gaa tgt      739
Tyr Ser Ile Ile Arg Arg Ser Ile Gln Thr Pro Glu Glu Asp Glu Cys
200                 205                 210                 215 cct cat tcc aag aaa ctc tgt cct att gac atg ctg tgg gat aac acc      787
Pro His Ser Lys Lys Leu Cys Pro Ile Asp Met Leu Trp Asp Asn Thr
                220                 225                 230 aaa tgt aaa tgt gtt ttg caa gac gag act cca ctg cct ggg aca gaa      835
Lys Cys Lys Cys Val Leu Gln Asp Glu Thr Pro Leu Pro Gly Thr Glu
            235                 240                 245 gac cac tct tac ctc cag gaa ccc act ctc tgt gga ccg cac atg acg      883
Asp His Ser Tyr Leu Gln Glu Pro Thr Leu Cys Gly Pro His Met Thr
        250                 255                 260 ttt gat gaa gat cgc tgt gag tgc gtc tgt aaa gca cca tgt ccg gga      931
Phe Asp Glu Asp Arg Cys Glu Cys Val Cys Lys Ala Pro Cys Pro Gly
265                 270                 275 gat ctc att cag cac ccg gaa aac tgc agt tgc ttt gag tgc aaa gaa      979
Asp Leu Ile Gln His Pro Glu Asn Cys Ser Cys Phe Glu Cys Lys Glu
280                 285                 290                 295 agt ctg gag agc tgc tgc caa aag cac aag att ttt cac cca gac acc     1027
Ser Leu Glu Ser Cys Cys Gln Lys His Lys Ile Phe His Pro Asp Thr
                300                 305                 310 tgc agg tca atg gtc ttt tcg ctt tcc cct taacttggtt tactgatgac       1077
Cys Arg Ser Met Val Phe Ser Leu Ser Pro
            315                 320 atttaaagga catactaatc tgatctgttc aggctctttt ctctcagagt ccaagcac      1135
```

<210> SEQ ID NO 4
<211> LENGTH: 321
<212> TYPE: PRT
<213> ORGANISM: Murinae gen. sp.

<400> SEQUENCE: 4

```
Met Tyr Gly Glu Trp Gly Met Gly Asn Ile Leu Met Met Phe His Val
  1               5                  10                  15

Tyr Leu Val Gln Gly Phe Arg Ser Glu His Gly Pro Val Lys Arg Ser
             20                  25                  30

Ser Arg Ser Met Leu Glu Arg Ser Glu Gln Gln Ile Arg Ala Ala Ser
```

```
                35                  40                  45
Ser Leu Glu Glu Leu Leu Gln Ile Ala His Ser Glu Asp Trp Lys Leu
 50                  55                  60
Trp Arg Cys Arg Leu Lys Leu Lys Ser Leu Ala Ser Met Asp Ser Arg
 65                  70                  75                  80
Ser Ala Ser His Arg Ser Thr Arg Phe Ala Ala Thr Phe Tyr Asp Thr
                 85                  90                  95
Glu Thr Leu Lys Val Ile Asp Glu Glu Trp Gln Arg Thr Gln Cys Ser
                100                 105                 110
Pro Arg Glu Thr Cys Val Glu Val Ala Ser Glu Leu Gly Lys Thr Thr
                115                 120                 125
Asn Thr Phe Phe Lys Pro Pro Cys Val Asn Val Phe Arg Cys Gly Gly
130                 135                 140
Cys Cys Asn Glu Glu Gly Val Met Cys Met Asn Thr Ser Thr Ser Tyr
145                 150                 155                 160
Ile Ser Lys Gln Leu Phe Glu Ile Ser Val Pro Leu Thr Ser Val Pro
                165                 170                 175
Glu Leu Val Pro Val Lys Ile Ala Asn His Thr Gly Cys Lys Cys Leu
                180                 185                 190
Pro Thr Gly Pro Arg His Pro Tyr Ser Ile Ile Arg Arg Ser Ile Gln
                195                 200                 205
Thr Pro Glu Glu Asp Glu Cys Pro His Ser Lys Lys Leu Cys Pro Ile
210                 215                 220
Asp Met Leu Trp Asp Asn Thr Lys Cys Lys Cys Val Leu Gln Asp Glu
225                 230                 235                 240
Thr Pro Leu Pro Gly Thr Glu Asp His Ser Tyr Leu Gln Glu Pro Thr
                245                 250                 255
Leu Cys Gly Pro His Met Thr Phe Asp Glu Asp Arg Cys Glu Cys Val
                260                 265                 270
Cys Lys Ala Pro Cys Pro Gly Asp Leu Ile Gln His Pro Glu Asn Cys
                275                 280                 285
Ser Cys Phe Glu Cys Lys Glu Ser Leu Glu Ser Cys Cys Gln Lys His
                290                 295                 300
Lys Ile Phe His Pro Asp Thr Cys Arg Ser Met Val Phe Ser Leu Ser
305                 310                 315                 320
Pro

<210> SEQ ID NO 5
<211> LENGTH: 5
<212> TYPE: PRT
<213> ORGANISM: Murinae gen. sp.

<400> SEQUENCE: 5

Asp Phe Ser Phe Glu
 1               5

<210> SEQ ID NO 6
<211> LENGTH: 110
<212> TYPE: PRT
<213> ORGANISM: Murinae gen. sp.

<400> SEQUENCE: 6

Thr Phe Tyr Asp Thr Glu Thr Leu Lys Val Ile Asp Glu Glu Trp Gln
 1               5                  10                  15
Arg Thr Gln Cys Ser Pro Arg Glu Thr Cys Val Glu Val Ala Ser Glu
                 20                  25                  30
```

-continued

```
Leu Gly Lys Thr Thr Asn Thr Phe Phe Lys Pro Pro Cys Val Asn Val
        35                  40                  45

Phe Arg Cys Gly Gly Cys Cys Asn Glu Glu Gly Val Met Cys Met Asn
        50                  55                  60

Thr Ser Thr Ser Tyr Ile Ser Lys Gln Leu Phe Glu Ile Ser Val Pro
 65              70                  75                      80

Leu Thr Ser Val Pro Glu Leu Val Pro Val Lys Ile Ala Asn His Thr
                85                  90                  95

Gly Cys Lys Cys Leu Pro Thr Gly Pro Arg His Pro Tyr Ser
            100             105             110
```

METHOD FOR ACTIVATING ONLY THE VASCULAR ENDOTHELIAL GROWTH FACTOR RECEPTOR-3 AND USES THEREOF

BACKGROUND OF THE INVENTION

The invention generally relates to a method for activating only the vascular endothelial growth factor receptor-3 (VEGFR-3) using mouse vascular endothelial growth factor-D (VEGF-D), and a method for promoting and maintaining lymphatic vascularization of tissue.

The two major components of the mammalian vascular system are the endothelial and smooth muscle cells. The endothelial cells form the lining of the inner surface of all blood vessels and lymphatic vessels in the mammal. The formation of new blood vessels can occur by two different processes, vasculogenesis or angiogenesis (for review see Risau, W., Nature 386: 671–674, 1997). Vasculogenesis is characterized by the in situ differentiation of endothelial cell precursors to mature endothelial cells and association of these cells to form vessels, such as occurs in the formation of the primary vascular plexus in the early embryo. In contrast, angiogenesis, the formation of blood vessels by growth and branching of pre-existing vessels, is important in later embryogenesis and is responsible for the blood vessel growth which occurs in the adult. Angiogenesis is a physiologically complex process involving proliferation of endothelial cells, degradation of extracellular matrix, branching of vessels and subsequent cell adhesion events. In the adult, angiogenesis is tightly controlled and limited under normal circumstances to the female reproductive system. However angiogenesis can be switched on in response to tissue damage. Importantly solid tumors are able to induce angiogenesis in surrounding tissue, thus sustaining tumor growth and facilitating the formation of metastases (Folkman, J., Nature Med. 1: 27–31, 1995). The molecular mechanisms underlying the complex angiogenic processes are far from being understood.

Lymphatic vessels are very different in structure from arteriae, veins and capillaries. Lymph vessels are characterized by an extremely permeable, thin endothelial lining devoid of a basal lamina. Simple end-to-end cell junctions and interdigitating and especially junctions between endothelial cells are a characteristic feature of lymphatic vessels. In addition, the lymphatics typically lack supporting cells, such as pericytes and smooth muscle cells (Leak, L., Microvasc Res 2: 361–391, 1970; Leak, L., J Cell Biol., 50: 300–323, 1971; and Leak and Jamuar, Am Rev Respir Dis. 128: S59–S65, 1983). The differences in the structure and cellular composition of lymphatic and non-lymphatic vessels suggest that the lymphatic endothelial cells may represent a very differentiated form of endothelial cells (Taiplae, J. et al., Cur. Topics Micro. Immunol. 237: 85–96, 1999).

A major function of the lymphatic system is to provide fluid return from tissues and to transport many extravascular substances back to the blood. In addition, during the process of maturation, lymphocytes leave the blood, migrate through lymphoid organs and other tissues, and enter the lymphatic vessels, and return to the blood through the thoracic duct. Specialized venules, high endothelial venules (HEVs), bind lymphocytes again and cause their extravasation into tissues. The lymphatic vessels, and especially the lymph nodes, thus play an important role in immunology and in the development of metastasis of different tumors. Unlike blood vessels, the embryonic origin of the lymphatic system is not as clear and at least three different theories exist as to its origin. Lymphatic vessels are difficult to identify due to the absence of known specific markers available for them.

Lymphatic vessels are most commonly studied with the aid of lymphography. In lymphography, X-ray contrast medium is injected directly into a lymphatic vessel. The contrast medium gets distributed along the efferent drainage vessels of the lymphatic system and is collected in the lymph nodes. The contrast medium can stay for up to half a year in the lymph nodes, during which time X-ray analyses allow the follow-up of lymph node size and architecture. This diagnostic is especially important in cancer patients with metastases in the lymph nodes and in lymphatic malignancies, such as lymphoma. However, improved materials and methods for imaging lymphatic tissues are needed in the art.

Angiogenesis is also involved in a number of pathologic conditions, where it plays a role or is involved directly in different sequelae of the disease. Some examples include neovascularization associated with various liver diseases, neovascular sequelae of diabetes, neovascular sequelae to hypertension, neovascularization in post-trauma, neovascularization due to head trauma, neovascularization in chronic liver infection (e.g. chronic hepatitis), neovascularization due to heat or cold trauma, dysfunction related to excess of hormone, creation of hemangiomas and restenosis following angioplasty.

Because of the crucial role of angiogenesis in so many physiological and pathological processes, factors involved in the control of angiogenesis have been intensively investigated. A number of growth factors have been shown to be involved in the regulation of angiogenesis; these include fibroblast growth factors (FGFs), platelet-derived growth factor (PDGF), transforming growth factor alpha (TGFα), and hepatocyte growth factor (HGF). See for example Folkman et al., J. Biol. Chem., 267: 10931–10934, 1992 for a review.

It has been suggested that a particular family of endothelial cell-specific growth factors, the vascular endothelial growth factors (VEGFs), and their corresponding receptors is primarily responsible for stimulation of endothelial cell growth and differentiation, and for certain functions of the differentiated cells. These factors are members of the PDGF/VEGF family, and appear to act primarily via endothelial receptor tyrosine kinases (RTKs). The PDGF/VEGF family of growth factors belongs to the cystine-knot superfamily of growth factors, which also includes the neurotrophins and transforming growth factor-β.

Eight different proteins have been identified in the PDGF/VEGF family, namely two PDGFs (A and B), VEGF and five members that are closely related to VEGF. The five members closely related to VEGF are: VEGF-B, described in International Patent Application PCT/US96/02957 (WO 96/26736) and in U.S. Pat. Nos. 5,840,693 and 5,607,918 by Ludwig Institute for Cancer Research and The University of Helsinki; VEGF-C or VEGF2, described in Joukov et al., EMBO J., 15: 290–298, 1996, Lee et al., Proc. Natl. Acad. Sci. USA, 93: 1988–1992, 1996, and U.S. Pat. Nos. 5,932,540 and 5,935,540 by Human Genome Sciences, Inc; VEGF-D, described in International Patent Application No. PCT/US97/14696 (WO 98/07832), and Achen et al., Proc. Natl. Acad. Sci. USA, 95: 548–553, 1998; the placenta growth factor (PlGF), described in Maglione et al., Proc. Natl. Acad. Sci. USA, 88: 9267–9271, 1991; and VEGF3, described in International Patent Application No. PCT/US95/07283 (WO 96/39421) by Human Genome Sciences, Inc. Each VEGF family member has between 30% and 45% amino acid sequence identity with VEGF. The VEGF family members share a VEGF homology domain which contains the six cysteine residues which form the cystine-knot motif. Functional characteristics of the VEGF family include varying degrees of mitogenicity for endothelial cells, induction of vascular permeability and angiogenic and lymphangiogenic properties.

Vascular endothelial growth factor (VEGF) is a homodimeric glycoprotein that has been isolated from several sources. Alterative mRNA splicing of a single VEGF gene gives rise to five isoforms of VEGF. VEGF shows highly specific mitogenic activity for endothelial cells. VEGF has important regulatory functions in the formation of new blood vessels during embryonic vasculogenesis and in angiogenesis during adult life (Carmeliet et al., Nature, 380: 435–439, 1996; Ferrara et al., Nature, 380: 439–442, 1996; reviewed in Ferrara and Davis-Smyth, Endocrine Rev., 18: 4–25, 1997). The significance of the role played by VEGF has been demonstrated in studies showing that inactivation of a single VEGF allele results in embryonic lethality due to failed development of the vasculature (Carmeliet et al., Nature, 380: 435–439, 1996; Ferrara et al., Nature, 380: 439–442, 1996). The isolation and properties of VEGF have been reviewed; see Ferrara et al., J. Cellular Biochem., 47: 211–218, 1991 and Connolly, J. Cellular Biochem., 47: 219–223, 1991.

In addition VEGF has strong chemoattractant activity towards monocytes, can induce the plasminogen activator and the plasminogen activator inhibitor in endothelial cells, and can also induce microvascular permeability. Because of the latter activity, it is sometimes referred to as vascular permeability factor (VPF). VEGF is also chemotactic for certain hematopoetic cells. Recent literature indicates that VEGF blocks maturation of dendritic cells and thereby reduces the effectiveness of the immune response to tumors (many tumors secrete VEGF) (Gabrilovich et al., Blood 92: 4150–4166, 1998; Gabrilovich et al., Clinical Cancer Research 5: 2963–2970, 1999).

VEGF-B has similar angiogenic and other properties to those of VEGF, but is distributed and expressed in tissues differently from VEGF. In particular, VEGF-B is very strongly expressed in heart, and only weakly in lung, whereas the reverse is the case for VEGF. This suggests that VEGF and VEGF-B, despite the fact that they are co-expressed in many tissues, may have functional differences.

VEGF-B was isolated using a yeast co-hybrid interaction trap screening technique by screening for cellular proteins which might interact with cellular retinoic acid-binding protein type I (CRABP-I). Its isolation and characteristics are described in detail in PCT/US96/02957 and in Olofsson et al., Proc. Natl. Acad. Sci. USA, 93: 2576–2581, 1996.

VEGF-C was isolated from conditioned media of the PC-3 prostate adenocarcinoma cell line (CRL1435) by screening for ability of the medium to produce tyrosine phosphorylation of the endothelial cell-specific receptor tyrosine kinase VEGFR-3 (Flt4), using cells transfected to express VEGFR-3. VEGF-C was purified using affinity chromatography with recombinant VEGFR-3, and was cloned from a PC-3 cDNA library. Its isolation and characteristics are described in detail in Joukov et al., EMBO J., 15: 290–298, 1996.

VEGF-D was isolated from a human breast cDNA library, commercially available from Clontech, by screening with an expressed sequence tag obtained from a human cDNA library designated "Soares Breast 3NbHBst" as a hybridization probe (Achen et al., Proc. Natl. Acad. Sci. USA, 95: 548–553, 1998). Its isolation and characteristics are described in detail in International Patent Application No. PCT/US97/14696 (WO98/07832).

In PCT/US97/14696, the isolation of a biologically active fragment of VEGF-D, designated VEGF-DΔNΔC, is also described. This fragment consists of VEGF-D amino acid residues 93 to 201 linked to the affinity tag peptide FLAG®. The entire disclosure of the International Patent Application PCT/US97/14696 (WO 98/07832) is incorporated herein by reference.

The VEGF-D gene is broadly expressed in the adult human, but is certainly not ubiquitously expressed. VEGF-D is strongly expressed in heart, lung and skeletal muscle. Intermediate levels of VEGF-D are expressed in spleen, ovary, small intestine and colon, and a lower expression occurs in kidney, pancreas, thymus, prostate and testis. No VEGF-D mRNA was detected in RNA from brain, placenta, liver or peripheral blood leukocytes.

PlGF was isolated from a term placenta cDNA library. Its isolation and characteristics are described in detail in Maglione et al., Proc. Natl. Acad. Sci. USA, 88: 9267–9271, 1991. Presently its biological function is not well understood.

VEGF3 was isolated from a cDNA library derived from colon tissue. VEGF3 is stated to have about 36% identity and 66% similarity to VEGF. The method of isolation of the gene encoding VEGF3 is unclear and no characterization of the biological activity is disclosed.

Similarity between two proteins is determined by comparing the amino acid sequence and conserved amino acid substitutions of one of the proteins to the sequence of the second protein, whereas identity is determined without including the conserved amino acid substitutions.

As noted above, the PDGF/VEGF family members act primarily by binding to receptor tyrosine kinases. In general, receptor tyrosine kinases are glycoproteins, which consist of an extracellular domain capable of binding a specific growth factor(s), a transmembrane domain, which is usually an alpha-helical portion of the protein, a juxtamembrane domain, which is where the receptor may be regulated by, e.g., protein phosphorylation, a tyrosine kinase domain, which is the enzymatic component of the receptor and a carboxy-terminal tail, which in many receptors is involved in recognition and binding of the substrates for the tyrosine kinase.

Five endothelial cell-specific receptor tyrosine kinases have been identified, belonging to two distinct subclasses: three vascular endothelial cell growth factor receptors, VEGFR-1 (Flt-1), VEGFR-2 (KDR/Flk-1), VEGFR-3 (Flt4), and the two receptors of the Tie family, Tie and Tie-2 (Tek). These receptors differ in their specificity and affinity. All of these have the intrinsic tyrosine kinase activity which is necessary for signal transduction. The VEGFRs are subclass-III receptor tyrosine kinases, homologous to the platelet-derived growth factor-receptor family, having seven immunoglobulin homology domains in the extracellular domain and a tyrosine kinase intracellular domain split by kinase insert sequence.

The only receptor tyrosine kinases known to bind VEGFs are VEGFR-1, VEGFR-2 and VEGFR-3. VEGFR-1 and VEGFR-2 bind VEGF with high affinity, and VEGFR-1 also binds VEGF-B and PlGF. VEGF-C has been shown to be the ligand for VEGFR-3, and it also activates VEGFR-2 (Joukov et al., The EMBO Journal, 15: 290–298, 1996). VEGF-D binds to both VEGFR-2 and VEGFR-3 (Achen et al., Proc. Natl. Acad. Sci. USA, 95: 548–553, 1998). A ligand for Tie-2 (Tek) has been described in International Patent Application No. PCT/US95/12935 (WO 96/11269) by Regeneron Pharmaceuticals, Inc. The ligand for Tie has not yet been identified.

Recently, a novel 130–135 kDa VEGF isoform specific receptor has been purified and cloned (Soker et al., *Cell,* 92: 735–745, 1998). The VEGF receptor was found to specifically bind the $VEGF_{165}$ isoform via the exon 7 encoded sequence, which shows weak affinity for heparin (Soker et al., *Cell,* 92: 735–745, 1998). Surprisingly, the receptor was shown to be identical to human neuropilin-1 (NP-1), a receptor involved in early stage neuromorphogenesis. PlGF-2 also appears to interact with NP-1 (Migdal et al., *J. Biol. Chem.,* 273: 22272–22278, 1998).

VEGFR-1, VEGFR-2 and VEGFR-3 are expressed differently by endothelial cells. Generally, both VEGFR-1 and VEGFR-2 are expressed in blood vessel endothelia (Oelrichs et al., *Oncogene,* 8: 11–18, 1992; Kaipainen et al., *J. Exp. Med.,* 178: 2077–2088, 1993; Dumont et al., *Dev. Dyn.,* 203: 80–92, 1995; Fong et al., *Dev. Dyn.,* 207: 1–10, 1996) and VEGFR-3 is mostly expressed in the lymphatic endothelium of adult tissues (Kaipainen et al., *Proc. Natl. Acad. Sci. USA,* 9: 3566–3570, 1995). VEGFR-3 is also expressed in the blood vasculature surrounding tumors.

Although VEGFR-1 is mainly expressed in endothelial cells during development, it can also be found in hematopoetic precursor cells during early stages of embryogenesis (Fong et al., *Nature,* 376: 66–70, 1995). In adults, monocytes and macrophages also express this receptor (Barleon et al., *Blood,* 87: 3336–3343, 1995). In embryos, VEGFR-1 is expressed by most, if not all, vessels (Breier et al., *Dev. Dyn.,* 204: 228–239, 1995; Fong et al., *Dev. Dyn.,* 207: 1–10, 1996).

The receptor VEGFR-3 is widely expressed on endothelial cells during early embryonic development but as embryogenesis proceeds becomes restricted to venous endothelium and then to the lymphatic endothelium (Kaipainen et al., *Cancer Res.,* 54: 6571–6577, 1994; Kaipainen et al., *Proc. Natl. Acad. Sci. USA,* 92: 3566–3570, 1995). VEGFR-3 is expressed on lymphatic endothelial cells in adult tissues. This receptor is essential for vascular development during embryogenesis.

The essential, specific role in vasculogenesis, angiogenesis and/or lymphangiogenesis of VEGFR-1, VEGFR-2, VEGFR-3, Tie and Tie-2 has been demonstrated by targeted mutations inactivating these receptors in mouse embryos. Disruption of the VEGFR genes results in aberrant development of the vasculature leading to embryonic lethality around midgestation. Analysis of embryos carrying a completely inactivated VEGFR-1 gene suggests that this receptor is required for functional organization of the endothelium (Fong et al., *Nature,* 376: 66–70, 1995). However, deletion of the intracellular tyrosine kinase domain of VEGFR-1 generates viable mice with a normal vasculature (Hiratsuka et al., *Proc. Natl. Acad. Sci. USA,* 95: 9349–9354, 1998). The reasons underlying these differences remain to be explained but suggest that receptor signalling via the tyrosine kinase is not required for the proper function of VEGFR-1. Analysis of homozygous mice with inactivated alleles of VEGFR-2 suggests that this receptor is required for endothelial cell proliferation, hematopoesis and vasculogenesis (Shalaby et al., *Nature,* 376: 62–66, 1995; Shalaby et al., *Cell,* 89: 981–990, 1997). Targeted inactivation of both copies of the VEGFR-3 gene in mice resulted in defective blood vessel formation characterized by abnormally organized large vessels with defective lumens, leading to fluid accumulation in the pericardial cavity and cardiovascular failure at post-coital day 9.5 (Dumont et al., *Science,* 282: 946–949, 1998). On the basis of these findings it has been proposed that VEGFR-3 is required for the maturation of primary vascular networks into larger blood vessels. However, the role of VEGFR-3 in the development of the lymphatic vasculature could not be studied in these mice because the embryos died before the lymphatic system emerged. Nevertheless it is assumed that VEGFR-3 plays a role in development of the lymphatic vasculature and lymphangiogenesis given its specific expression in lymphatic endothelial cells during embryogenesis and adult life. This is supported by the finding that ectopic expression of VEGF-C, a ligand for VEGFR-3, in the skin of transgenic mice, resulted in lymphatic endothelial cell proliferation and vessel enlargement in the dermis. Furthermore this suggests that VEGF-C may have a primary function in lymphatic endothelium, and a secondary function in angiogenesis and permeability regulation which is shared with VEGF (Joukov et al., *EMBO J.,* 15: 290–298, 1996).

Homologs of the human VEGF receptor-3 have been cloned from the mouse and quail (Finnerty, *Oncogene,* 8: 2293–2298, 1993; and Eichmann et al., *Gene,* 174: 3–8, 1996). They are relatively conserved in evolution, the quail having 70% amino acid identity with the human receptor and having similar ligand receptor binding.

There is tremendous interest in the development of pharmacological agents which could antagonize the receptor-mediated actions of VEGFs (Martiny-Baron and Marme, *Curr. Opin. Biotechnol.* 6: 675–680, 1995). Monoclonal antibodies to VEGF have been shown to suppress tumor growth in vivo by inhibiting tumor-associated angiogenesis (Kim et al., *Nature* 362: 841–844, 1993). Similar inhibitory effects on tumor growth have been observed in model systems resulting from expression of either antisense RNA for VEGF (Saleh et al., *Cancer Res.* 56: 393–401, 1996) or a dominant-negative VEGFR-2 mutant (Millauer et al., *Nature* 367: 576–579, 1994).

However, tumor inhibition studies with neutralizing antibodies suggested that other angiogenic factors besides VEGF may be involved (Kim, K. et al., *Nature* 362: 841–844, 1993). Furthermore, the activity of angiogenic factors other than VEGF in malignant melanoma is suggested by the finding that not all melanomas express VEGF (Issa, R. et al., *Lab Invest* 79: 417–425, 1999).

The biological functions of the different members of the VEGF family are currently being elucidated. Of particular interest are the properties of VEGF-D and VEGF-C. These proteins bind to both VEGFR-2 and VEGFR-3, localized on vascular and lymphatic endothelial cells, respectively. They are also closely related in primary structure (48% amino acid identity). Both factors are mitogenic for endothelial cells in vitro. Recently, VEGF-C was shown to be angiogenic in the mouse cornea model and in the avian chorioallantoic membrane (Cao et al., *Proc. Natl. Acad. Sci. USA* 95: 14389–14394, 1998) and was able to induce angiogenesis in the setting of tissue ischemia (Witzenbichler et al., *Am. J. Pathol.* 153: 381–394, 1998). Furthermore, VEGF-C stimulated lymphangiogenesis in the avian chorioallantoic membrane (Oh et al., *Dev. Biol.* 188: 96–109, 1997) and in a transgenic mouse model (Jeltsch et al., *Science* 276: 1423–1425, 1997). VEGF-D was shown to be angiogenic in the rabbit cornea (Marconcini et al., *Proc. Natl. Acad. Sci. USA* 96: 9671–9676, 1999). The lymphangiogenic capacity of VEGF-D has not yet been reported, however, given that VEGF-D, like VEGF-C, binds and activates VEGFR-3, a receptor thought to signal for lymphangiogenesis (Taipale et al., *Cur. Topics Micro. Immunol.* 237: 85–96, 1999), it is highly likely that VEGF-D is lymphangiogenic. VEGF-D and VEGF-C may be of particular importance for the malignancy of tumors, as metastases can spread via either blood vessels or lymphatic vessels; therefore molecules which stimulate angiogenesis or lymphangiogenesis could contribute toward malignancy. This has already been shown to be the case for VEGF. It is noteworthy that VEGF-D gene expression is induced by c-Fos, a transcription factor known to be important for malignancy (Orlandini et al., *Proc. Natl. Acad. Sci. USA* 93: 11675–11680, 1996). It is speculated that the mechanism by which c-Fos contributes to malignancy is the upregulation of genes encoding angiogenic factors. Tumor cells deficient in c-fos fail to undergo malignant progression, possibly due to an inability to induce angiogenesis (Saez, E. et al., *Cell* 82: 721–732, 1995). This indicates the existence of an angiogenic factor up-regulated by c-fos during tumor progression.

As shown in FIG. 1, the predominant intracellular form of human VEGF-D is a homodimeric propeptide that consists of the VEGF/PDGF Homology Domain (VHD) and the N- and C-terminal propeptides. After secretion, this polypeptide is proteolytically cleaved (Stacker, S. A. et al., *J Biol Chem* 274: 32127–32136, 1999). Proteolytic processing (at positions marked by black arrowheads) gives rise to partially processed forms and a fully processed, mature form which consists of dimers of the VHD. With human VEGF-D, the VHD consists of residues 93 to 201 of full length VEGF-D and contains the binding sites for both VEGFR-2 and VEGFR-3. The mature form binds both VEGFR-2 and VEGFR-3 with much higher affinity than the unprocessed form (Stacker, S. A. et al., *J Biol Chem* 274: 32127–32136, 1999).

The description of the cloning of the mouse homolog of VEGF-D is also found in International Patent Application PCT/US97/14696 (WO 98/07832). With the mouse, it was found that there are two isoforms. The longer amino acid sequence is designated mVEGF-D1, and the shorter sequence is designated mVEGF-D2. The nucleotide sequences of the cDNAs encoding mVEGF-D1 and mVEGF-D2 are found in SEQ ID NOs:1 and 3, respectively. The deduced amino acid sequences for mVEGF-D1 and mVEGF-D2 are found in SEQ ID NOs:2 and 4, respectively. The differences between the amino acid sequences are:

i) an insertion of five amino acids (DFSFE) (SEQ ID NO: 5) after residue 30 in mVEGF-D1 in comparison to mVEGF-D2;

ii) complete divergence of the C-terminal ends after residue 317 in mVEGF-D1 and residue 312 in mVEGF-D2, which results in mVEGF-D1 being considerably longer.

VEGF-D is highly conserved between mouse and man. 85% of the amino acid residues of human VEGF-D are identical in mouse VEGF-D1. It is also predicted that the predominant intracellular form of mouse VEGF-D is a homodimeric propeptide that consists of the VEGF/PDGF Homology Domain (VHD) and the N- and C-terminal propeptides. The mouse VHD consists of residues 92 to 201 (SEQ ID NO:6) of the full length mouse VEGF-D2 (SEQ ID NO:4).

SUMMARY OF THE INVENTION

The invention generally relates to a method for promoting and/or maintaining lymphatic vascularization of tissue that involves activation of only the vascular endothelial growth factor receptor-3 (VEGFR-3) using mouse vascular endothelial growth factor-D (VEGF-D).

According to a first aspect, the invention provides a method for stimulating proliferation and/or maintaining of only lymph vessel endothelial cells. The method comprises administering to the endothelial cells an effective amount of a composition comprising a polypeptide with the amino acid sequence of SEQ ID NO:2 or SEQ ID NO:4 or SEQ ID NO:6 or a fragment thereof. Preferably the polypeptide has at least 90%, and more preferably at least 95% identity to the amino acid sequence of SEQ ID NO:2 or SEQ ID NO:4 or SEQ ID NO:6 or a fragment thereof.

As herein used the term "fragment thereof" refers to fragments of a polypeptide having at least a 90% sequence identity to the amino acid sequence of SEQ ID NO:2 or SEQ ID NO:4 or SEQ ID NO:6 and that has the ability to only stimulate one or more of lymphatic vessel endothelial cells to proliferate, differentiate, migrate or survive.

According to a second aspect, the invention provides a method for activation of only the VEGF receptor-3 which comprises administering to a cell bearing this receptor an effective amount of a composition comprising a polypeptide having the amino acid sequence of SEQ ID NO:2 or SEQ ID NO:4 or SEQ ID NO:6 or a fragment thereof. Preferably the polypeptide has at least 90%, and more preferably at least 95% identity to the amino acid sequence of SEQ ID NO:2 or SEQ ID NO:4 or SEQ ID NO:6 or a fragment thereof. This method can be carried out in vivo or in vitro.

Since the polypeptide specifically activates the VEGF receptor-3, this polypeptide can be used to stimulate endothelial cell proliferation in a situation where VEGF receptor-2 is not activated. Accordingly, the invention provides for a method for specific activation of VEGF receptor-3 and not the VEGF receptor-2.

In addition, variant forms of the mouse VEGF-D polypeptide which result from naturally-occurring allelic variants of the nucleic acid sequence encoding mouse VEGF-D are encompassed within the scope of the invention. Allelic variants are well known in the art, and represent alternative forms or a nucleic acid sequence which comprise substitution, deletion or addition of one or more nucleotides, but which do not result in any substantial functional alteration of the encoded polypeptide.

Where amino acid substitution is used to create a variant, the substitution is conservative, i.e. an amino acid is replaced by one of similar size and with similar charge properties.

As used herein, the term "conservative substitution" denotes the replacement of an amino acid residue by another, biologically similar residue. Examples of conservative substitutions include the substitution of one hydrophobic residue such as isoleucine, valine, leucine, alanine, cysteine, glycine, phenylalanine, proline, tryptophan, tyrosine, norleucine or methionine for another, or the substitution of one polar residue for another, such as the substitution of arginine for lysine, glutamic acid for aspartic acid, or glutamine for asparagine, and the like. Neutral hydrophilic amino acids which can be substituted for one another include asparagine, glutamine, serine and threonine. The term "conservative substitution" also includes the use of a substituted amino acid in place of an unsubstituted parent amino acid.

As such, it should be understood that in the context of the present invention, a conservative substitution is recognized in the art as a substitution of one amino acid for another amino acid that has similar properties. Exemplary conservative substitutions are set out in the following Table A from WO 97/09433.

TABLE A

Conservative Substitutions I

| SIDE CHAIN CHARACTERISTIC | AMINO ACID |
| --- | --- |
| Aliphatic | G A P |
| Non-polar | I L V |
| Polar - uncharged | C S T M |
|  | N Q |
| Polar - charged | D E |
|  | K R |
| Aromatic | H F W Y |
| Other | N Q D E |

Alternatively, conservative amino acids can be grouped as described in Lehninger, [Biochemistry, Second Edition; Worth Publishers, Inc. New York, New York (1975), pp.71–77] as set out in the following Table B.

TABLE B

Conservative Substitutions II

| SIDE CHAIN CHARACTERISTIC | AMINO ACID |
| --- | --- |
| Non-polar (hydrophobic) | |
| A. Aliphatic: | A L I V P |
| B. Aromatic: | F W |
| C. Sulfur-containing: | M |
| D. Borderline: | G |
| Uncharged-polar | |
| A. Hydroxyl: | S T Y |
| B. Amides: | N Q |
| C. Sulfhydryl: | C |
| D. Borderline: | G |
| Positively Charged (Basic): | K R H |
| Negatively Charged (Acidic): | D E |

Exemplary conservative substitutions are set out in the following Table C.

TABLE C

Conservative Substitutions III

| Original Residue | Exemplary Substitution |
| --- | --- |
| Ala (A) | Val, Leu, Ile |
| Arg (R) | Lys, Gln, Asn |
| Asn (N) | Gln, His, Lys, Arg |
| Asp (D) | Glu |
| Cys (C) | Ser |
| Gln (Q) | Asn |
| Glu (E) | Asp |
| His (H) | Asn, Gln, Lys, Arg |
| Ile (I) | Leu, Val, Met, Ala, Phe, |
| Leu (L) | Ile, Val, Met, Ala, Phe |
| Lys (K) | Arg, Gln, Asn |
| Met (M) | Leu, Phe, Ile |
| Phe (F) | Leu, Val, Ile, Ala |
| Pro (P) | Gly |
| Ser (S) | Thr |
| Thr (T) | Ser |
| Trp (W) | Tyr, Phe |
| Tyr (Y) | Trp, Phe, Thr, Ser |
| Val (V) | Ile, Leu, Met, Phe, Ala |

As used herein, the term "mouse VEGF-D" collectively refers to the polypeptide having the amino acid of SEQ ID NO:2 or SEQ ID NO:4 or SEQ ID NO:6 and fragments thereof and other variants which have the biological activity of mouse VEGF-D as herein defined. Those skilled in the art will recognize that there is considerable latitude in amino acid sequence charges which can occur naturally or be engineered without affecting biological activity of the polypeptide. It is preferred that the variant polypeptides be at least 90% and more preferably be at least 95% identical to the amino acid sequence of SEQ ID NO:2 or SEQ ID NO:4 or SEQ ID NO:6 and fragments thereof. Percent sequence identity is determined by conventional methods. See, for example, Altschul et al, Bull. Math. Bio., 1986 48 603–616 and Henikoff and Henikoff, Proc. Natl. Acad. Sci. USA, 1992 89 10915–10919.

The polypeptide having at least a 90% identity with the amino acid sequence of SEQ ID NO:2 or SEQ ID NO:4 or SEQ ID NO:6 or a fragment thereof may be employed in combination with a suitable pharmaceutical carrier. The resulting compositions comprise a therapeutically effective amount of the claimed polypeptide, and a pharmaceutically acceptable non-toxic salt thereof, and a pharmaceutically acceptable solid or liquid carrier or adjuvant. Examples of such a carrier or adjuvant include, but are not limited to, saline, buffered saline, Ringer's solution, mineral oil, talc, corn starch, gelatin, lactose, sucrose, microcrystalline cellulose, kaolin, mannitol, dicalcium phosphate, sodium chloride, alginic acid, dextrose, water, glycerol, ethanol, thickeners, stabilizers, suspending agents and combinations thereof. Such compositions may be in the form of solutions, suspensions, tablets, capsules, creams, salves, elixirs, syrups, wafers, ointments or other conventional forms. The formulation to suit the mode of administration. Compositions comprising a polypeptide having at least a 90% identity with the amino acid sequence of SEQ ID NO:2 or SEQ ID NO:4 or SEQ ID NO:6 or a fragment thereof will contain from about 0.1% to 90% by weight of the active compound, and most generally from about 10% to 30%.

For intramuscular preparations, a sterile formulation, preferably a suitable soluble salt form of the claimed polypeptide, such as hydrochloride salt, can be dissolved and administered in a pharmaceutical diluent such as pyrogen-free water (distilled), physiological saline or 5% glucose solution. A suitable insoluble form of the compound may be prepared and administered as a suspension in an aqueous base or a pharmaceutically acceptable oil base, e.g. an ester of a long chain fatty acid such as ethyl oleate.

According to a third aspect, the invention provides a method for screening for and/or diagnosing a neoplastic disease characterized by a change in lymph vessel endothelial cells. The method comprises obtaining a sample from an animal suspected of being in a disease state characterized by an increase in lymph vessel endothelial cells; exposing said a polypeptide comprising an amino acid sequence having at least a 90% identity with the amino acid sequence of SEQ ID NO:2 or SEQ ID NO:4 or SEQ ID NO:6 or a fragment thereof; washing said sample; and screening for said disease by detecting the presence, quantity or distribution of VEGF receptor-3 in said sample, where detection of an increase in expression of VEGF receptor-3 in or on lymph vessel endothelial cells in or around a potential neoplastic growth is indicative of a neoplastic disease.

It is clearly understood that for the purposes of this specification the term "sample" includes, but is not limited to, a tissue sample, blood, serum, plasma, urine, ascities fluid or pleural effusion. Preferably the tissue is human tissue.

Polypeptides according to the invention may be labeled with a detectable label, and utilized to identify the VEGF receptor-3 in situ. The polypeptide may be covalently or non-covalently coupled to a suitable supermagnetic, paramagnetic, electron dense, ecogenic or radioactive agent for imaging. For use in diagnostic assays, radioactive or non-radioactive labels may be used. Examples of radioactive labels include a radioactive atom or group, such as $^{125}I$ or $^{32}P$. Examples of non-radioactive labels include enzymatic labels, such as horseradish peroxidase or fluorimetric labels, such as fluorescein-5-isothiocyanate (FITC). Labeling may be direct or indirect, covalent or non-covalent.

It will be clearly understood that for the purposes of this specification the word "comprising" means "including but not limited to". The corresponding meaning applies to the word "comprises".

DETAILED DESCRIPTION OF PREFERRED EMBODIMENTS

EXAMPLE 1

Expression and Purification of Mouse VEGF-D

To test the receptor binding properties of mouse VEGF-D, a plasmid was constructed for expression of the VEGF Homology Domain (VHD) of mouse VEGF-D. A DNA fragment encoding amino acid residues 92 to 201 (SEQ ID NO:6) of full-length mouse VEGF-D2 (SEQ ID NO:4) was amplified by polymerase chain reaction (PCR) with Pfu DNA polymerase, using as template a plasmid comprising full-length mouse VEGF-D cDNA (SEQ ID NOs:1 or 3). The amplified DNA fragment, the correctness of which was confirmed by nucleotide sequencing, was then inserted into the expression vector pEFBOSSFLAG (a gift from Dr. Clare McFarlane at the Walter and Eliza Hall Institute for Medical Research (WEHI), Melbourne, Australia). The pEFBOSS-FLAG vector contains DNA encoding the signal sequence for protein secretion from the murine interleukin-3 (IL-3) gene and the FLAG® octapeptide (IBI/Kodak). The FLAG® octapeptide can be recognized by commercially available antibodies such as the M2 monoclonal antibody (IBI/Kodak). The VEGF-D PCR fragment was inserted into the vector such that the IL-3 signal sequence was immediately upstream from the FLAG® octapeptide, which was in turn immediately upstream from the truncated VEGF-D sequence. All three sequences were in the same reading frame, so that translation of mRNA resulting from transfection of pEFBOSSFLAG-mouseVEGF-DΔNΔC into mammalian cells would give rise to a protein which would have the IL-3 signal sequence at its N-terminus, followed by the FLAG® octapeptide and the truncated VEGF-D sequence. Cleavage of the signal sequence and subsequent secretion of the protein from the cell would give rise to a VEGF-D polypeptide which is tagged with the FLAG® octapeptide adjacent to the N-terminus. This protein was designated mouse VEGF-DΔNΔC. The expression cassette encoding the FLAG-tagged truncated VEGF-D construct was subcloned into the pAPEX-3 expression vector and then transiently expressed in 293EBNA-1 cells using Fugene (Boehringer Mannheim) mediated transfection. After seven days of incubation, the conditioned medium was collected (approximately 150 ml) and subjected to affinity chromatography using the M2 (anti-FLAG) beads (IBI/Kodak) according to the manufacturer.

SDS-PAGE and Immunoblotting

Figure 1:
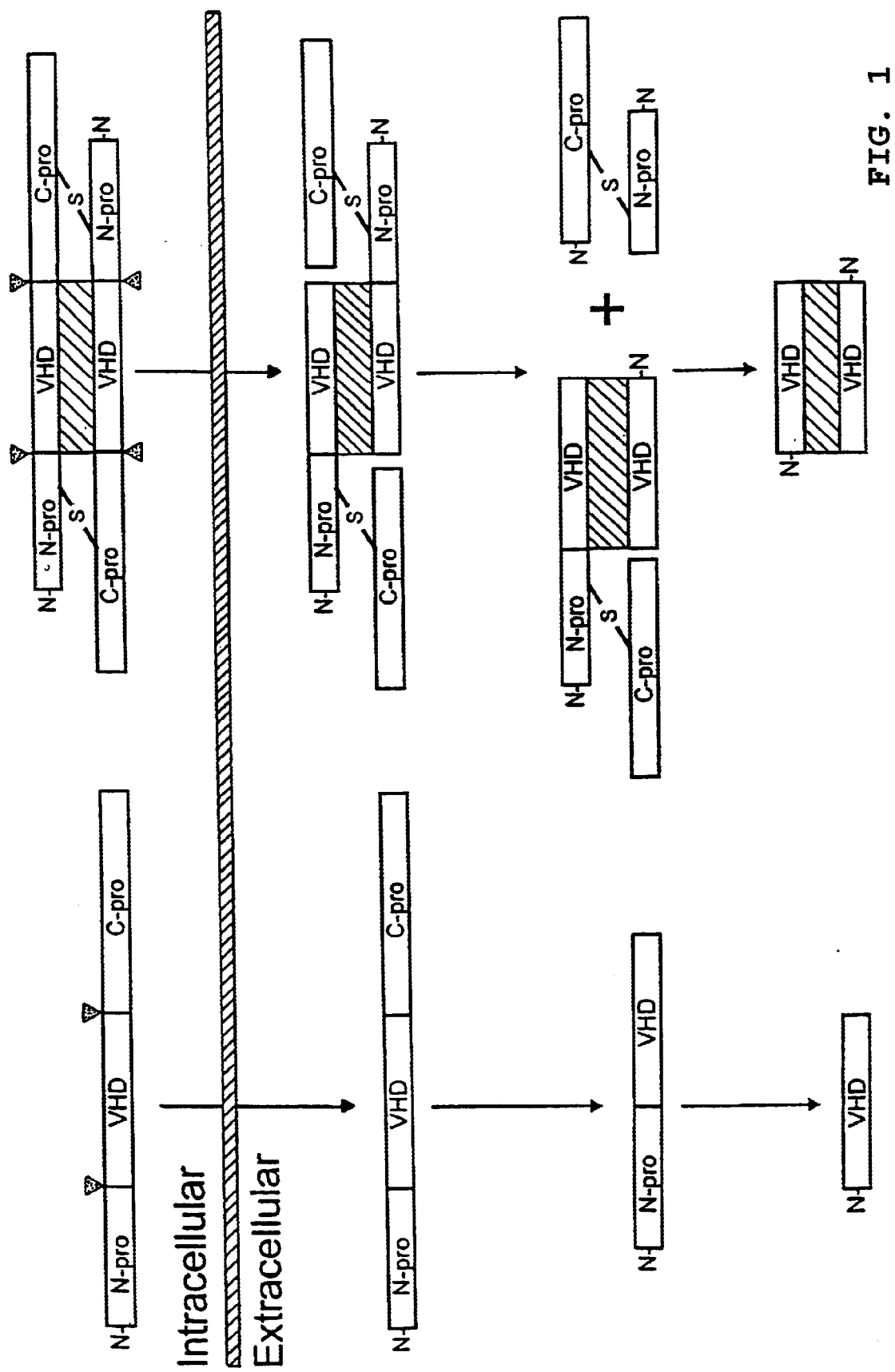
FIG. 1 is a schematic representation of VEGF-D processing.
Figure 2:
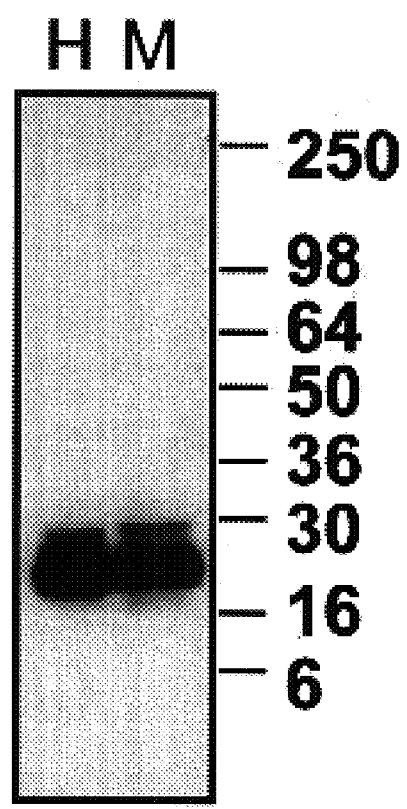
FIG. 2 shows the results of Western blot analyis of human (H) and mouse (M) VEGF-DΔNΔC.

Mouse VEGF-DΔNΔC arising from affinity chromatography and purified human VEGF-DΔNΔC (for comparison purposes) were analyzed by Western blotting. About 50 ng of each protein was separately combined with SDS-PAGE sample buffer under reducing (2% β-mercaptoethanol) conditions, boiled and resolved by SDS-PAGE. The proteins were transferred to nitrocellulose and blotted with M2 antibody. As seen in FIG. 2, both human and mouse VEGF-DΔNΔC subunits have the expected molecular weight of 22 kDa.

EXAMPLE 2

Bioassay for Mouse VEGF-DΔNΔC Binding to VEGF Receptors-2 and -3

Figure 3:
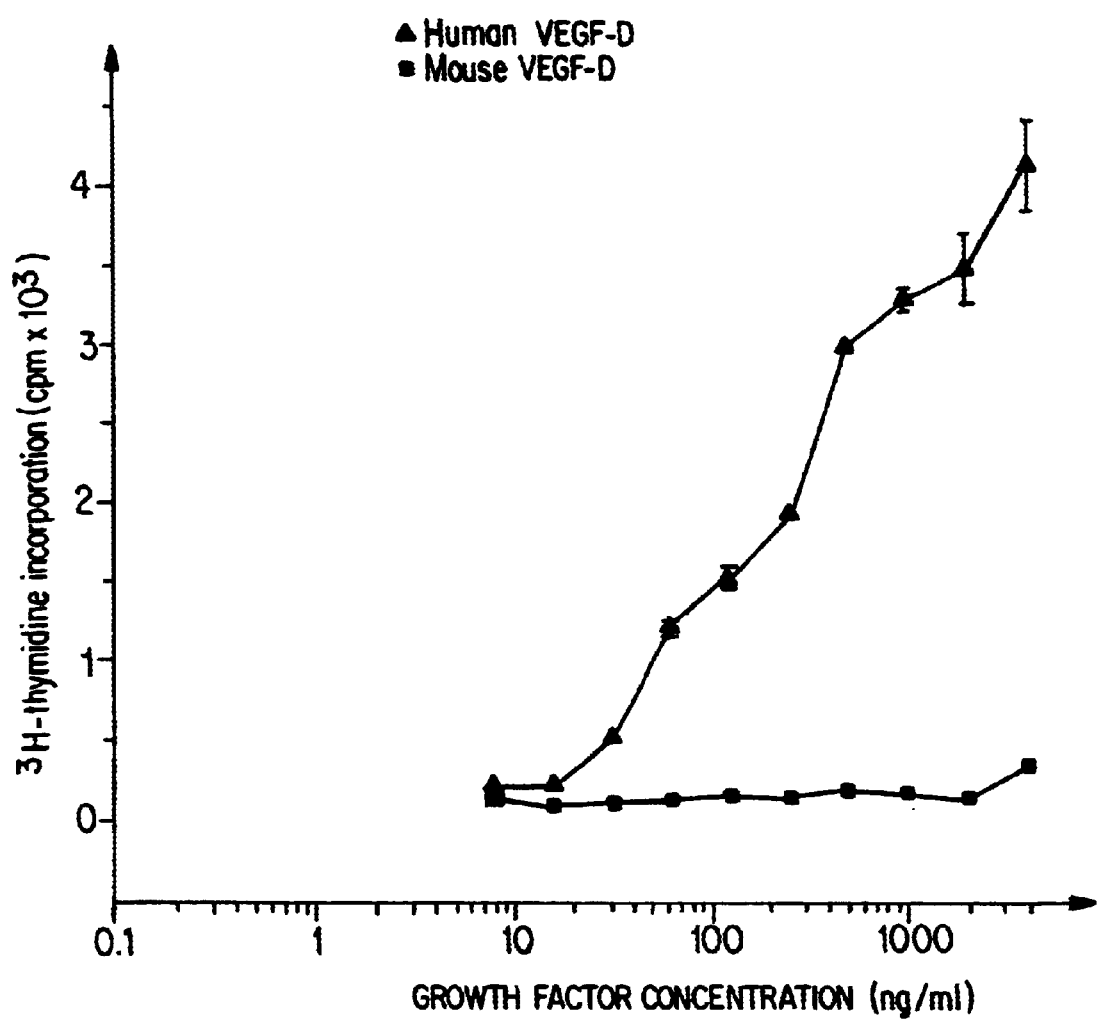
FIG. 3 shows the results of the VEGFR-2 bioassay using human and mouse VEGF-DΔNΔC.
Figure 4:
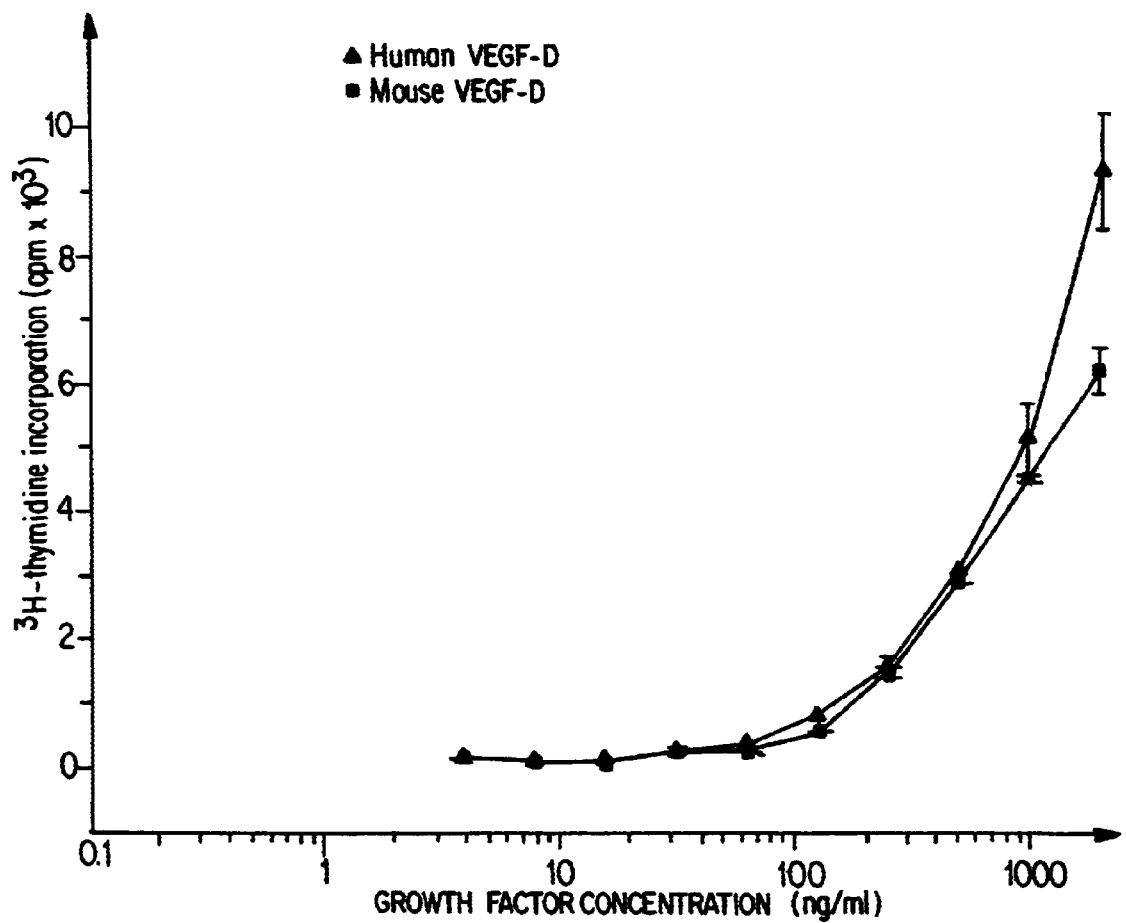
FIG. 4 shows the results of the VEGFR-3 bioassay using human and mouse VEGF-DΔNΔC.

The capacity of mouse VEGF-DΔNΔC to bind and cross-link VEGFR-2 and VEGFR-3 was tested in bioassays. FIGS. 3 and 4 shows the results of analysis of mouse VEGF-DΔNΔC protein using a VEGFR-2/-3 bioassay, respectively. The bioassay was performed using Ba/F3 cells which express a chimeric receptor consisting of the extracellular domain of mouse VEGFR-2 or human VEGFR-3 and the transmembrane and cytoplasmic domains of the mouse erythropoietin receptor (EpoR). These cell lines die in the absence of IL-3, unless they are supplied with ligands that cross-link the chimeric receptors. Cross-linking of the VEGFR/EpoR chimeric receptors induces signaling from the EpoR cytoplasmic domains that stimulates cell survival and proliferation.

The cells were maintained in Dulbecco's Modified Eagle Medium(DMEM) containing 10% fetal bovine serum (FBS), 50 mM L-glutamine, 50 μg/ml gentamicin and 10% of the Walter and Eliza Hall Institute of Medical Research (WEHI)-3D-conditioned medium as a source of interleukin-3 (IL-3) Cells expressing the VEGFR-2-EpoR or VEGFR-3-EpoR chimeric receptor were washed three times in phosphate buffered saline (PBS), and once in complete medium lacking IL-3. Cells ($10^4$) were aliquoted into 96-well microtiter plates containing dilutions of the test reagent or medium alone. Cells were incubated for 48 hours at 37° C. in a humidified atmosphere of 5% $CO_2$. Cell proliferation was quantified by the addition of 1 μCi of $^3H$-thymidine for four hours prior to harvesting. Incorporation of $^3H$-thymidine was determined using a cell harvester and β-counting.

As mentioned above, activation of the chimeric receptor rescues the cells from their dependence on IL-3 and causes the cells to proliferate in the absence of IL-3. Human VEGF-DΔNΔC which is a ligand for both VEGFR-2 and VEGFR-3, stimulates growth of these cell lines in a specific and dose-dependent fashion (see FIGS. 3 and 4, respectively). Mouse VEGF-DΔNΔC was able to simulate growth of VEGFR-3/EpoR cell line in a specific and dose-dependent fashion, but had no significant effect on the VEGFR-2/EpoR cell line even at a concentration as high as 4 μg/ml (see FIGS. 4 and 3, respectively). Assays were carried out in duplicate and error bars denote a standard deviation of +/−1.0. This unexpected finding demonstrates that mouse VEGF-DΔNΔC is not an activating ligand for VEGFR-2. Note that the VEGFR-2 extracellular domain in the chimeric VEGFR-2/EpoR receptor expressed in the Ba/F3-VEGFR-2-EpoR cell line was derived from mouse VEGFR-2. Therefore the inability of mouse VEGF-DΔNΔC to induce survival and proliferation of these cells was not due to a species difference between this ligand and the extracellular domain of the chimeric receptor.

The foregoing description and examples have been set forth merely to illustrate the invention and are not intended to be limiting. Since modifications of the disclosed embodiments incorporating the spirit and substance of the invention may occur to persons skilled in the art, the invention should be construed broadly to include all variations falling within the scope of the appended claims and equivalents thereof.

What is claimed is:

1. A method for stimulating proliferation and/or maintaining of only lymph vessel endothelial cells, in a mammal in need of such treatment, comprising:

administering to said cells an effective amount of a composition comprising a polypeptide having at least a 90% sequence identity with the amino acid sequence of SEQ ID NO:2 or SEQ ID NO:4 or SEQ ID NO:6, or a fragment thereof which has the ability to only stimulate lymphatic vessel endothelial cells to proliferate, differentiate, migrate or survive.

2. The method of claim 1, wherein the polypeptide has at least a 95% sequence identity with the amino acid sequence of SEQ ID NO:2 or SEQ ID NO:4 or SEQ ID NO:6, or a fragment thereof.

3. The method of claim 2, wherein the polypeptide comprises the amino acid sequence of SEQ ID NO:2 or SEQ ID NO:4 or SEQ ID NO:6, or a fragment thereof.

4. The method of claim 1, wherein the polypeptide comprises the amino acid sequence of SEQ ID NO:2 or SEQ ID NO:4 or SEQ ID NO:6.

5. A method for activating only a VEGF receptor-3, comprising:

administering to a cell bearing said receptor an effective amount of a composition comprising a polypeptide having at least 90% sequence identity with the amino acid sequence of SEQ ID NO:2 or SEQ ID NO:4 or SEQ ID NO:6, or a fragment thereof which has the ability only to activate a VEGF receptor 3.

6. The method of claim 5, wherein the polypeptide has a 95% sequence identity with the amino acid sequence of SEQ ID NO:2 or SEQ ID NO:4 or SEQ ID NO:6, or a fragment thereof.

7. The method of claim 6, wherein the polypeptide comprises the amino acid sequence of SEQ ID NO:2 or SEQ ID NO:4 or SEQ ID NO:6, or a fragment thereof.

8. The method of claim 7, wherein the polypeptide comprises the amino acid sequence of SEQ ID NO:2 or SEQ ID NO:4 or SEQ ID NO:6.

9. The method of claim 5, wherein the method is carried out in vivo.

10. The method of claim 5, wherein the method is carried out in vitro.

* * * * *